United States Patent [19]

Krämer et al.

[11] Patent Number: 4,563,447

[45] Date of Patent: * Jan. 7, 1986

[54] COMBATING FUNGI WITH 4-PIPERIDINO METHYL-1,3-DIOXOLANES

[75] Inventors: Wolfgang Krämer; Joachim Weissmüller; Dieter Berg, all of Wuppertal; Paul Reinecke, Leverkusen; Gerd Hänssler, Leverkusen; Wilhelm Brandes, Leichlingen, all of Fed. Rep. of Germany

[73] Assignee: Bayer Aktiengesellschaft, Leverkusen, Fed. Rep. of Germany

[*] Notice: The portion of the term of this patent subsequent to Mar. 5, 2002 has been disclaimed.

[21] Appl. No.: 630,487

[22] Filed: Jul. 13, 1984

[30] Foreign Application Priority Data

Aug. 4, 1983 [DE] Fed. Rep. of Germany ....... 3328151

[51] Int. Cl.$^4$ .................. A01N 43/40; C07D 405/06; C07D 405/13
[52] U.S. Cl. .................... 514/184; 546/207; 514/184; 514/326
[58] Field of Search ............ 546/207; 71/94; 514/184, 189, 326

[56] References Cited

U.S. PATENT DOCUMENTS 4,503,059  3/1985  Kramer et al. .............. 546/207

FOREIGN PATENT DOCUMENTS 0057864  1/1982  European Pat. Off. .......... 548/262
0056461  7/1982  European Pat. Off. .......... 546/216
0094167  11/1983 European Pat. Off. .......... 548/262
2095236  9/1982  United Kingdom ............. 548/262

OTHER PUBLICATIONS

Chemical Abstracts, vol. 90, No. 9, 2/26/79; Columbus, Ohio, USA.
Chemical Abstracts, vol. 95, No. 14, 10/5/81, Columbus, Ohio, USA.

Primary Examiner—Robert T. Bond
Attorney, Agent, or Firm—Sprung, Horn, Kramer & Woods

[57] ABSTRACT

Substituted 4-piperidinomethyl-1,3-dioxolanes of the formula

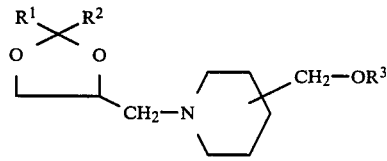

in which
$R^1$ is tetrahydronaphthyl, decahydronaphthyl, optionally substituted naphthyl, optionally substituted cycloalkyl or cycloalkenyl, optionally substituted phenyl, or alkyl which is substituted by in each case optionally substituted phenyl, phenoxy, phenylthio, cyclohexyl, cyclohexyloxy or cyclohexylthio,
$R^2$ is hydrogen or methyl,
$R^3$ is hydrogen or an acyl radical
or plant-tolerated addition products thereof with acids or metal salts, which possess fungicidal activity.

12 Claims, No Drawings

COMBATING FUNGI WITH 4-PIPERIDINO METHYL-1,3-DIOXOLANES

The invention relates to new substituted 4-piperidinomethyl-1,3-dioxolanes, a process for their preparation and their use as agents for combating pests.

It is already known that certain 1,3-dioxolanes, such as, for example 2-[1-(4-chlorophenoxy)-2-methylprop-2-yl]-4-ethyl-2-(1,2,4-triazol-1-ylmethyl)-1,3-dioxolane hydrochloride (see U.S. Ser. No. 343,054 filed Jan. 27, 1982 now U.S. Pat. No. 4,472,395, or organic sulphur compounds, such as, for example, zinc ethylene-1,2-bis-(dithiocarbamate) (compare R. Wegler, "Chemie der Pflanzenschutz- und Schädlingsbekämpfungsmittel" ("Chemistry of Plant Protection Agents and Agents for Combating Pests"), Springer Verlag, Berlin, Heidelberg, New York 1970, Volume 2, page 65 et seq.), have fungicidal properties.

However, under certain circumstances, especially when low amounts and concentrations are used, the action of these compounds is not always completely satisfactory in some fields of use.

New substituted 4-piperidinomethyl-1,3-dioxolanes of the general formula (I)

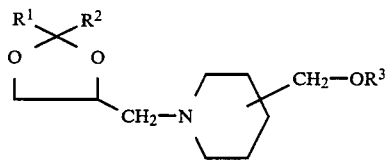

in which
- $R^1$ represents tetrahydronaphthyl, decahydronaphthyl, optionally substituted naphthyl, optionally substituted cycloalkyl or cycloalkenyl, optionally substituted phenyl, or alkyl which is substituted by in each case optionally substituted phenyl, phenoxy, phenylthio, cyclohexyl, cyclohexyloxy or cyclohexylthio,
- $R^2$ represents hydrogen or methyl and
- $R^3$ represents hydrogen or an acyl radical, and acid addition salts and metal salt complexes thereof which are tolerated by plants, have been found.

The compounds of the formula (I) can be obtained as geometric and/or optical isomers for isomer mixtures of varying compositions. Both the pure isomers and the isomer mixtures are obtained according to the invention.

It has furthermore been found that the new substituted 4-piperidinomethyl-1,3-dioxolanes of the general formula (I)

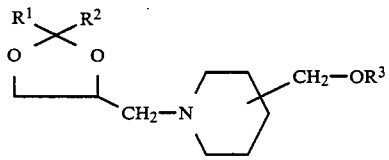

in which
- $R^1$ represents tetrahydronaphthyl, decahydronaphthyl, optionally substituted naphthyl, optionally substituted cycloalkyl or cycloalkenyl, optionally substituted phenyl, or alkyl which is substituted by in each case optionally substituted phenyl, phenoxy, phenylthio, cyclohexyl, cyclohexyloxy or cyclohexylthio,
- $R^2$ represents hydrogen or methyl and
- $R^3$ represents hydrogen or an acyl radical, and acid addition salts and metal salt complexes thereof which are tolerated by plants, are obtained by a process in which dioxolanes substituted in the 4-position, of the general formula (II)

in which
- $R^1$ and $R^2$ have the abovementioned meaning and
- X represents halogen or optionally substituted alkylsulphonyloxy or arylsulphonyloxy, are reacted with hydroxymethylpiperidines of the general formula (III)

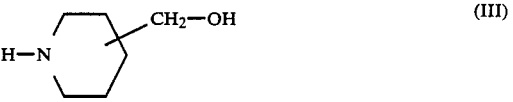

if appropriate in the presence of a diluent, if appropriate in the presence of a catalyst and if appropriate in the presence of an acid-binding agent, and, if appropriate, the resulting 4-(hydroxymethylpiperidinomethyl)1,3-dioxolanes according to the invention, of the general formula (Ia)

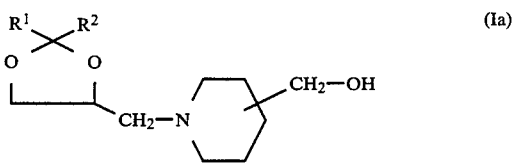

in which
- $R^1$ and $R^2$ have the abovementioned meanings, are acylated on the oxygen of the hydroxymethyl group in a second stage with an acylating agent in a manner which is known in principle, if appropriate in the presence of a diluent and if appropriate in the presence of an acid-binding agent, and, if appropriate, an acid or a metal salt is then added on.

It is also possible to quaternize the 4-piperidinomethyl-1,3-dioxolanes of the formula (I) according to the invention on the nitrogen by generally customary methods to give the corresponding tetra-substituted ammonium salts.

Finally, it has been found that the new substituted 4-piperidinomethyl-1,3-dioxolanes of the formula (I) have fungicidal properties.

Surprisingly, the compounds of the formula (I) according to the invention exhibit a more powerful fungicidal activity than the compounds known from the prior art, that is to say 2-[1-(4-chlorophenoxy)-2-methyl-yl-prop-2-yl]-4-ethyl-2-(1,2,4-triazol-1-yl-methyl)-1,3-dioxolane hydrochloride or zinc ethylene-1,2-bis-(dithiocarbamate), which are closely related compounds chemically and/or from the point of view of their action. The compounds according to the invention thus represent an enrichment of the art.

Formula (I) cites a general definition of the substituted 4-piperidinomethyl-1,3-dioxolanes according to the invention.

Preferred compounds of the formula (I) are those in which $R^1$ represents tetrahydronaphthyl, decahydronaphthyl, or naphthyl which is optionally mono- to hepta-substituted by identical or different substituents, possible substituents being: hydroxyl, halogen and in each case straight-chain or branched alkyl, alkoxy, alkenyloxy, alkinyloxy and alkanoylxy with in each case 1 to 4 carbon atoms in the alkyl part; or furthermore, represents cycloalkyl or cycloalkenyl with in each case 3 to 7 carbon atoms and in each case optionally mono- or poly-substituted by identical or different straight-chain or branched alkyl radicals with up to 4 carbon atoms, or represents phenyl which is optionally mono- or poly-substituted by identical or different substituents, or represents phenylalkyl, phenoxyalkyl or phenylthioalkyl with in each case up to 6 carbon atoms in the straight-chain or branched alkyl part, optionally mono- or poly-substituted in the phenyl nucleus by identical or different substituents, possible substituents on the phenyl in each case being: hydroxyl, halogen, cyano, nitro, in each case straight-chain or branched alkyl, alkoxy, alkenyloxy, alkinyloxy and alkylthio with in each case up to 4 carbon atoms, halogenoalkyl, halogenoalkoxy and halogenoalkylthio with in each case 1 or 2 carbon atoms and 1 to 5 identical or different halogen atoms, cycloalkyl with 5 to 7 carbon atoms, straight-chain or branched alkoxycarbonyl and alkanoyloxy with in each case up to 4 carbon atoms in the alkyl part, phenyl and phenoxy, optionally substituted by halogen, in particular fluorine or chlorine, or by straight-chain or branched alkyl with up to 4 carbon atoms, and the radical R-O-N=CH—, R representing straight-chain or branched alkyl, alkenyl or alkinyl with in each case up to 4 carbon atoms; or, in addition, represents cyclohexylalkyl, cyclohexyloxyalkyl or cyclohexylthioalkyl with in each case up to 6 carbon atoms in the straight-chain or branched alkyl parts and in each case optionally mono- or poly-substituted in the cyclohexyl part by identical or different straight-chain or branched alkyl radicals with up to 4 carbon atoms, $R^2$ represents hydrogen or methyl and $R^3$ represents hydrogen or a radical of the formula

wherein $R^4$ represents straight-chain or branched alkyl, alkoxy or alkylamino or dialkylamino with in each case 1 to 6 carbon atoms in the individual alkyl parts, straight-chain or branched alkoxyalkyl with in each case 1 to 6 carbon atoms in the two alkyl parts, straight-chain or branched halogenoalkyl with up to 6 carbon atoms and up to 5 identical or different halogen atoms or the furyl radical.

Particularly preferred compounds of the general formula (I) are those in which $R^1$ represents tetrahydronaphthyl, decahydronaphthyl, or naphthyl which is optionally mono-, di- or tri-substituted by identical or different substituents, possible substituents being: fluorine, chlorine, bromine, iodine, hydroxyl, methyl, ethyl, methoxy, ethoxy, allyloxy, propargyloxy and acetoxy, or, furthermore, cycloalkyl or cycloalkenyl with 5 to 7 carbon atoms, optionally mono-, di- or tri-substituted by identical or different methyl or ethyl radicals, or represents phenyl which is optionally mono-, di- or tri-substituted by identical or different substituents or a radical of the formula

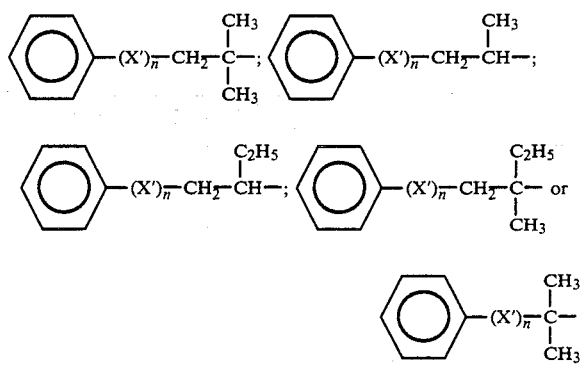

which is optionally mono-, di- or tri-substituted in the phenyl nucleus by identical or different substituents, possible substituents on the phenyl in each case being: hydroxyl, fluorine, chlorine, bromine, iodine, cyano, nitro, methyl, methoxy, methylthio, ethyl, ethoxy, ethylthio, n- and i-propyl, isopropoxy, n-, i-, s- and t-butyl, allyloxy, propargyloxy, trifluoromethyl, trifluoromethoxy, trifluoromethylthio, cyclohexyl, methoxycarbonyl, ethoxycarbonyl, acetoxy, and phenyl or phenoxy which is optionally substituted by fluorine, chlorine or methyl, and the radical R-O-N=CH—, R representing methyl, ethyl, n- or i-propyl, n-, i-, s- or t-butyl, allyl or propargyl; or, in addition, represents a radical of the formula

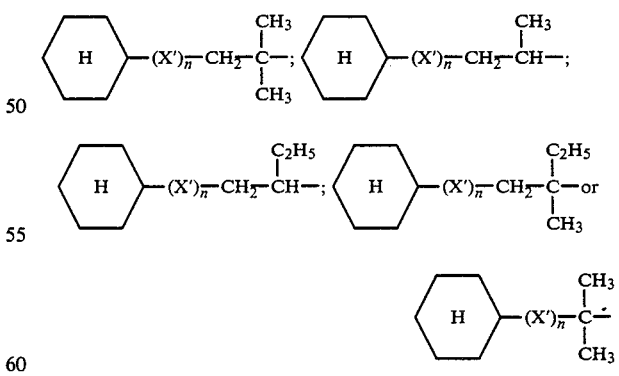

which is optionally mono- to tri-substituted in the cyclohexyl part by identical or different methyl, ethyl or isopropyl radicals, X' in each case representing oxygen or sulphur and n representing 0 or 1 in all of the radicals shown above by their formulae, $R^2$ represents methyl and $R^3$ represents hydrogen or a radical of the formula

wherein
R⁴ represents methyl, ethyl, n- or i-propyl, methoxymethyl, chloromethyl, dichloromethyl, trichloromethyl, methoxy, ethoxy, methylamino, ethylamino, dimethylamino, diethylamino or the furyl radical.
The following compounds of the general formula (I) may be mentioned specifically, in addition to the compounds mentioned in the preparation examples:
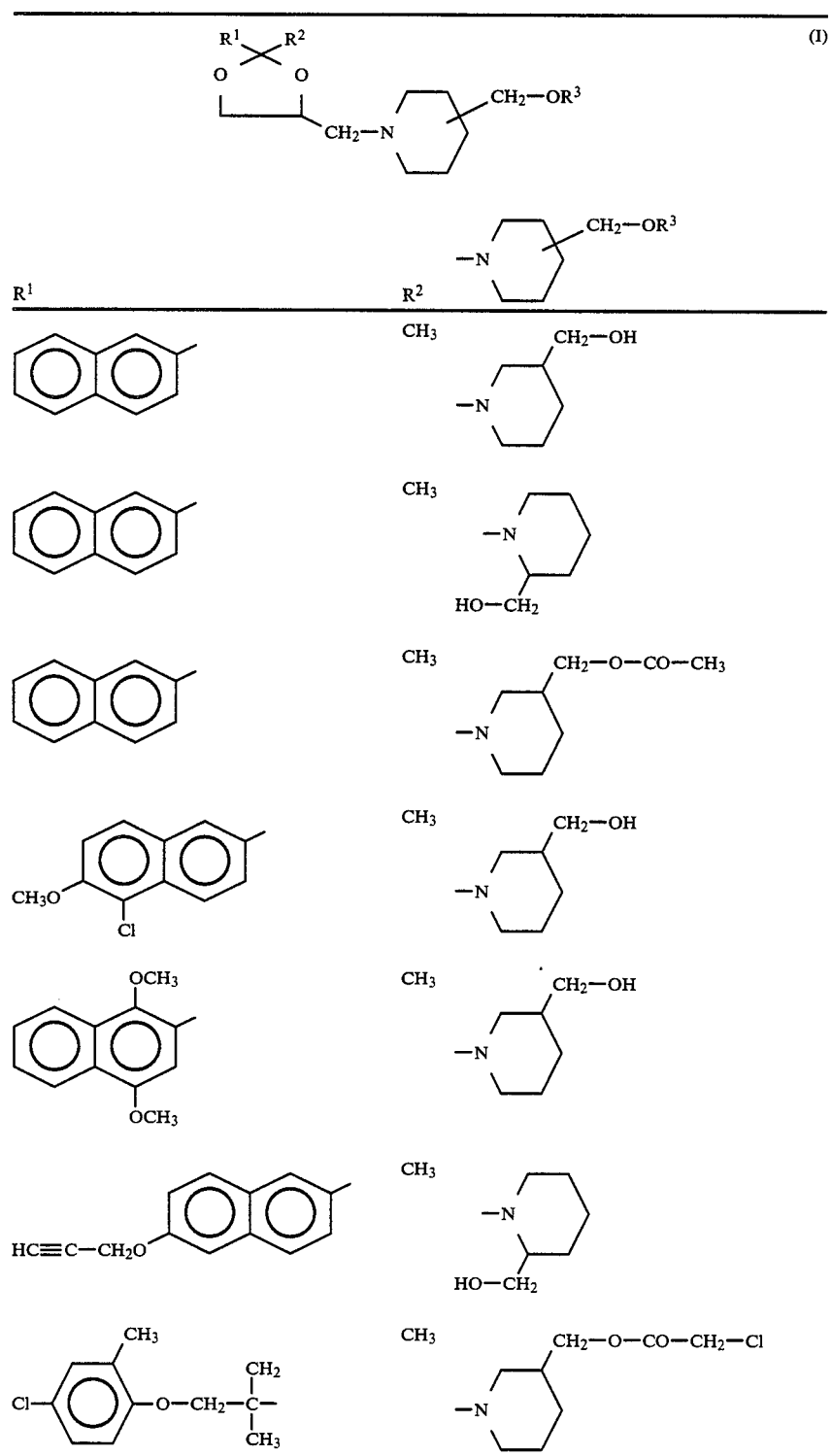

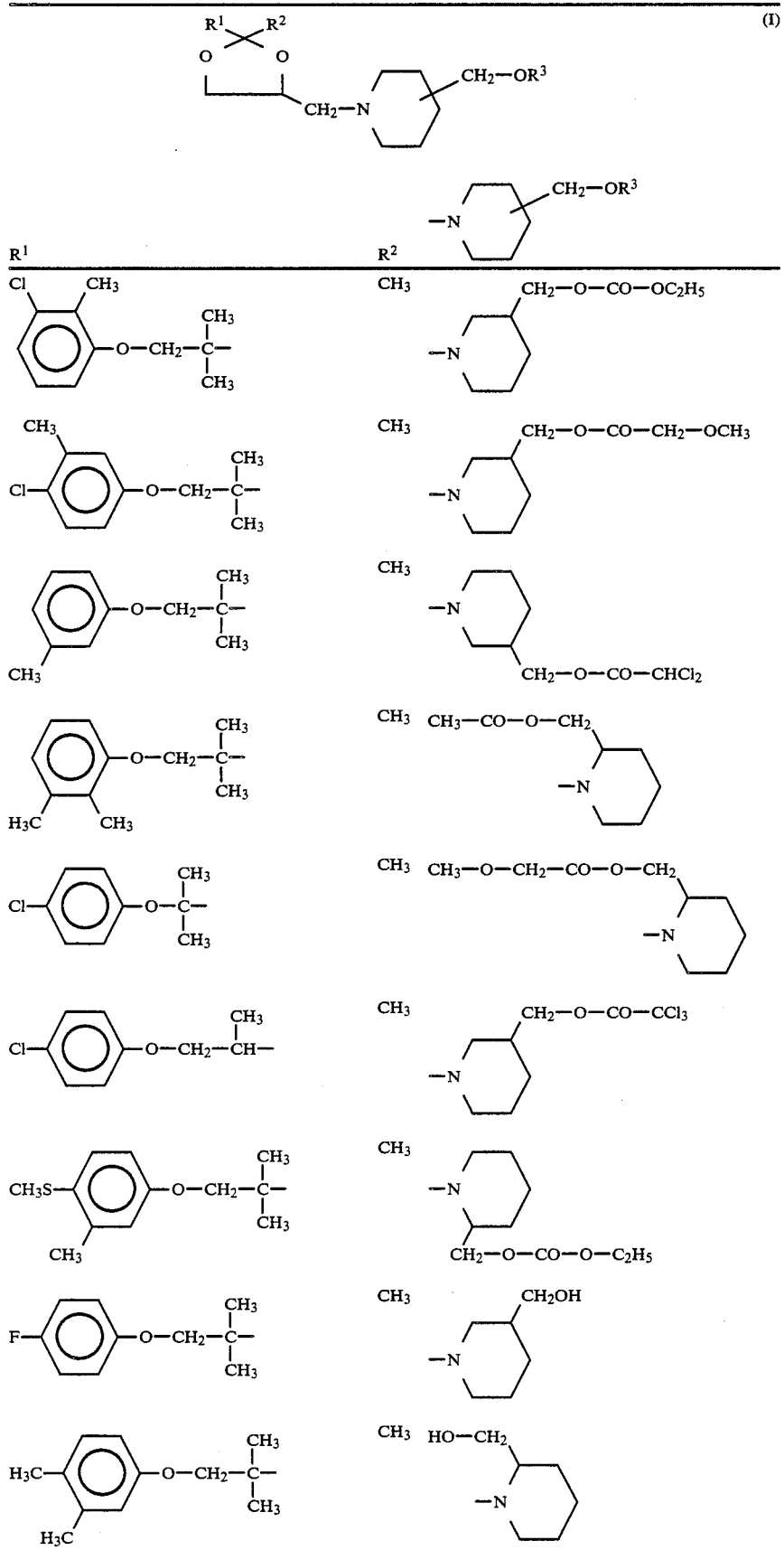

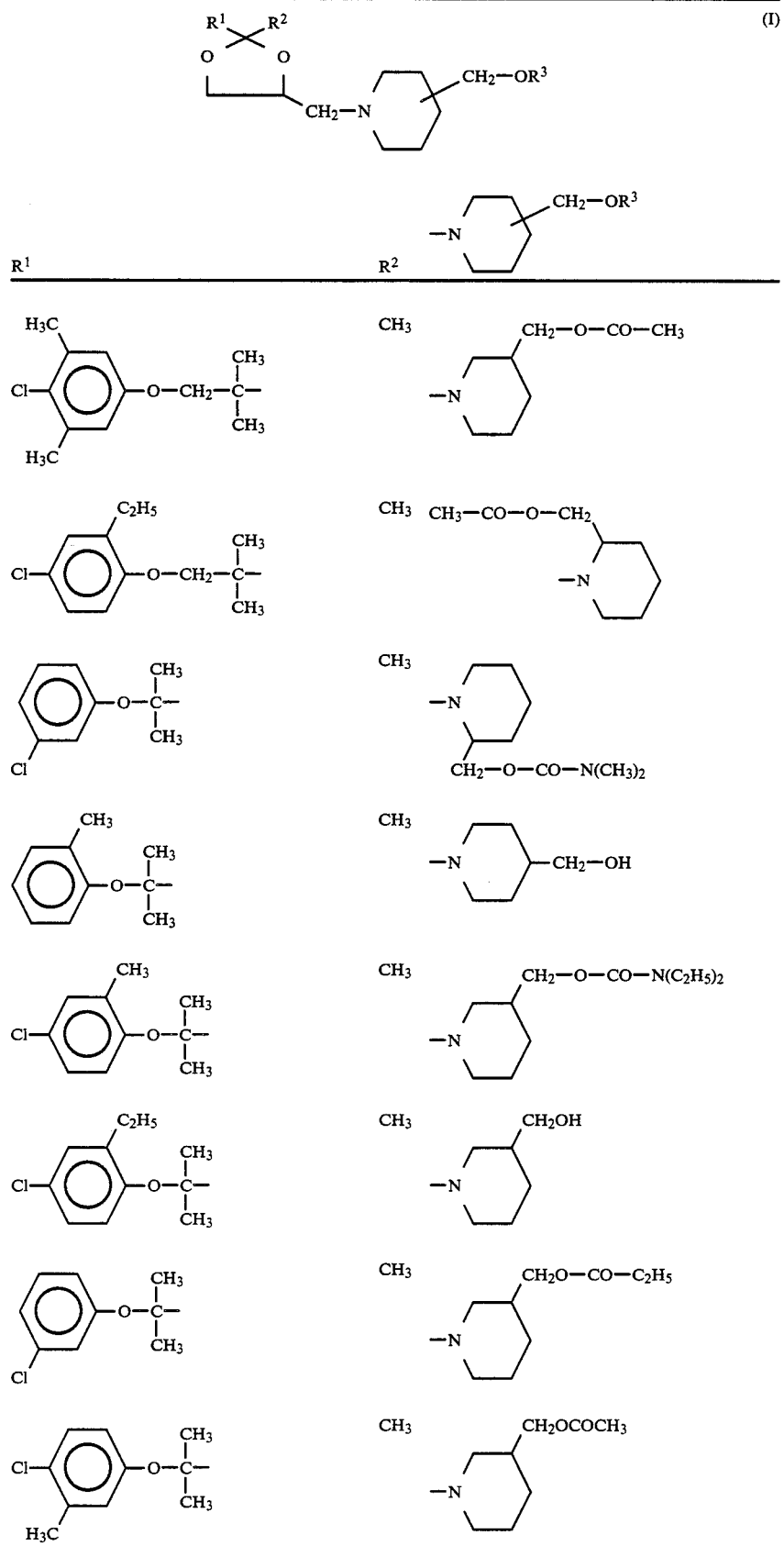

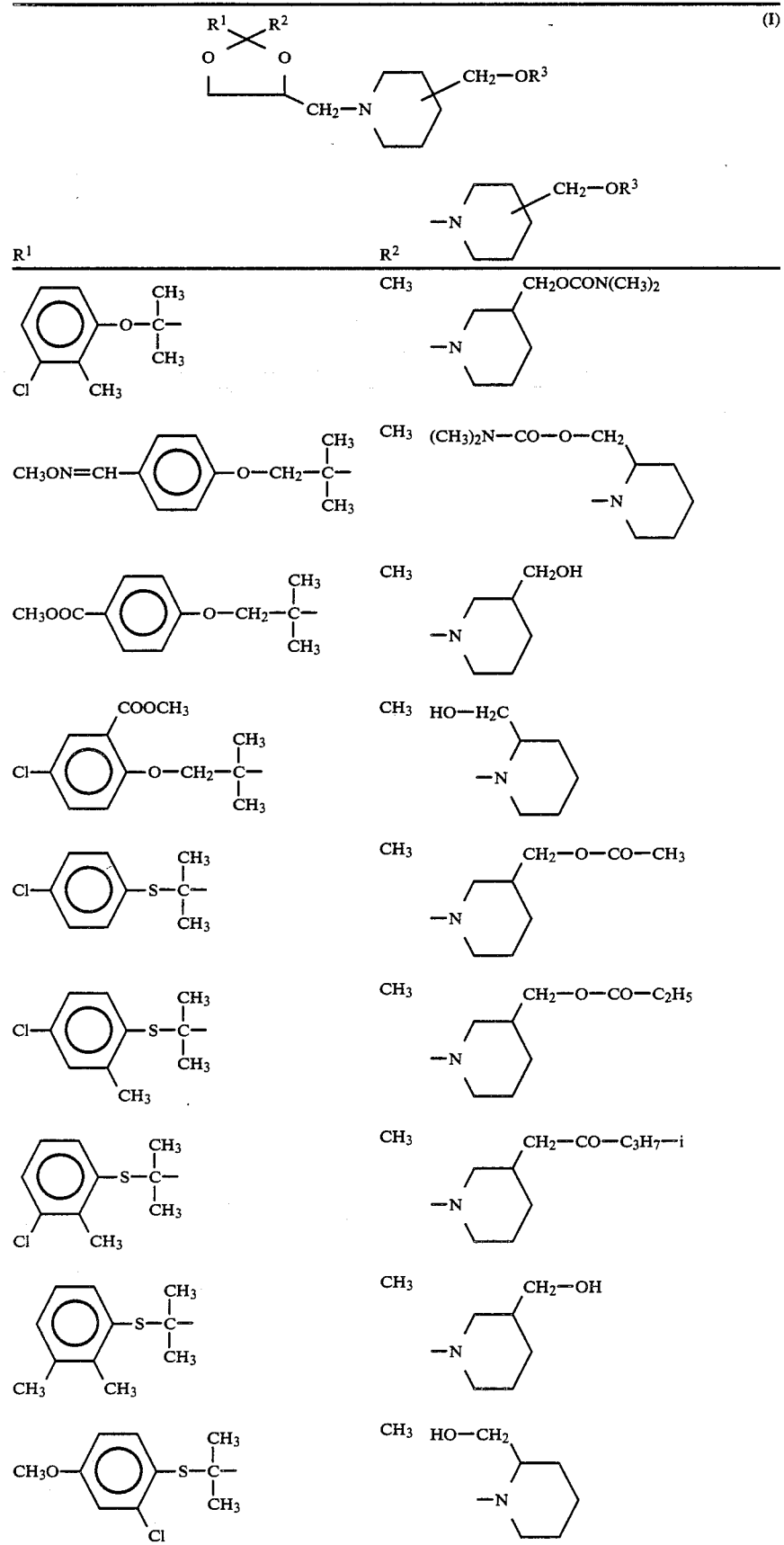

-continued
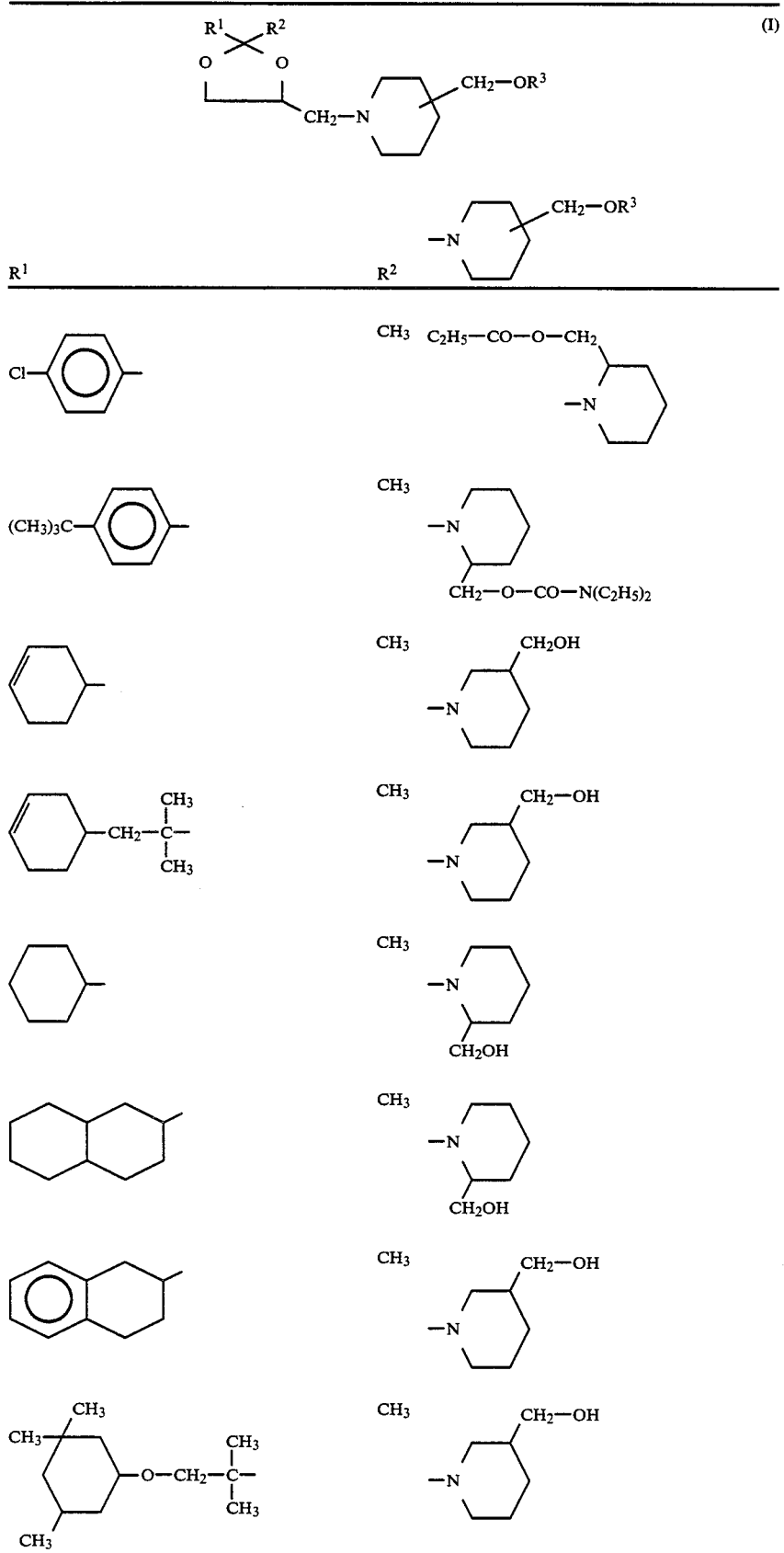

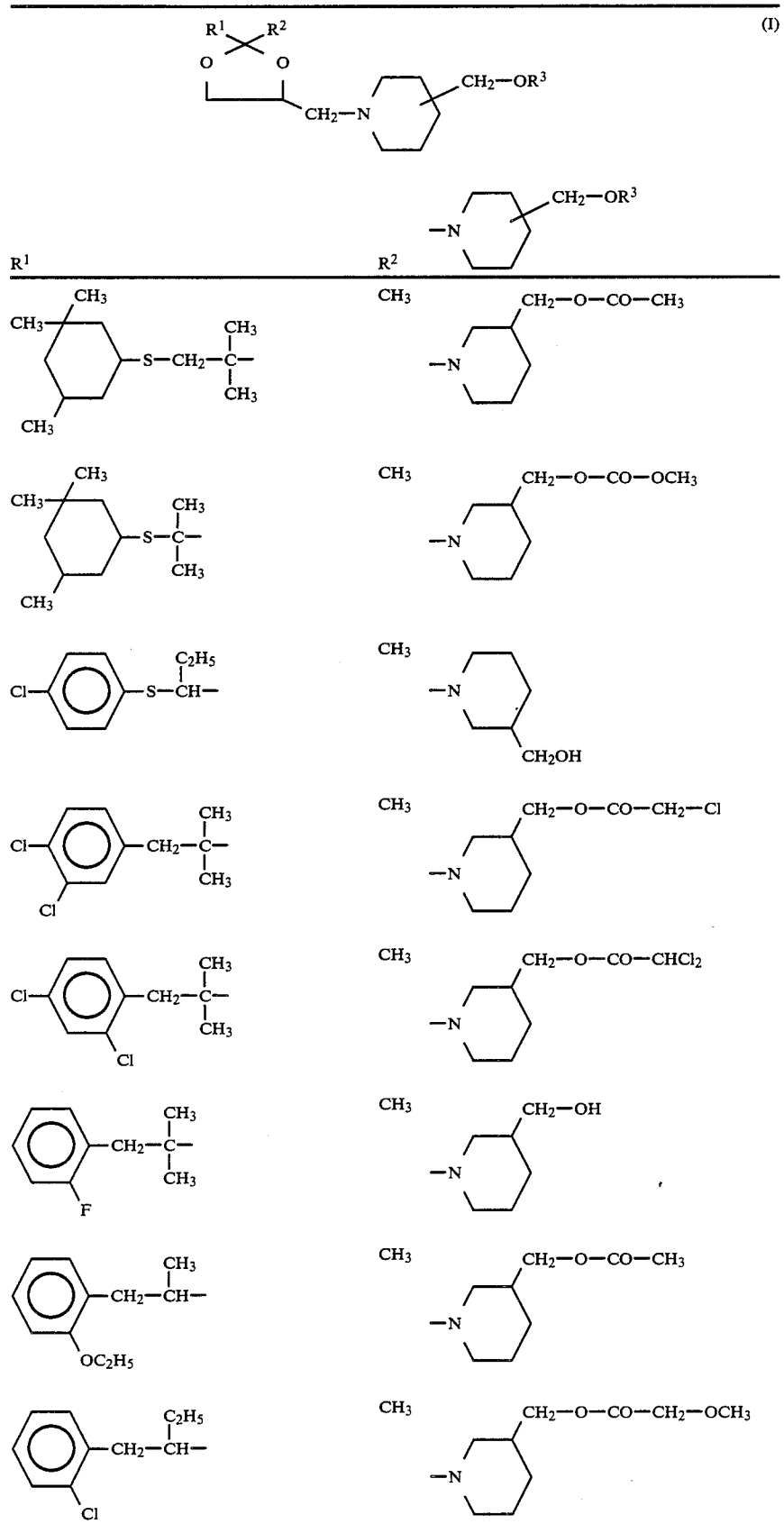

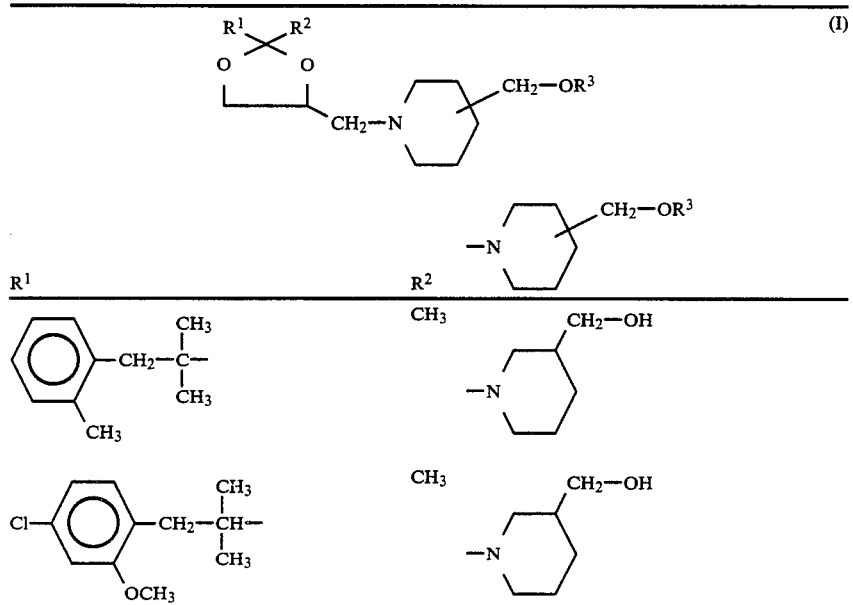

If, for example, 4-chloromethyl-2-[1-(4-chlorophenoxy)-2-methyl-prop-2-yl]-2-methyl-1,3-dioxolane and 3-hydroxymethylpiperidine are used as starting substances and acetyl chloride is used as the acylating agent, the course of the reaction in the process according to the invention can be represented by the following equation:

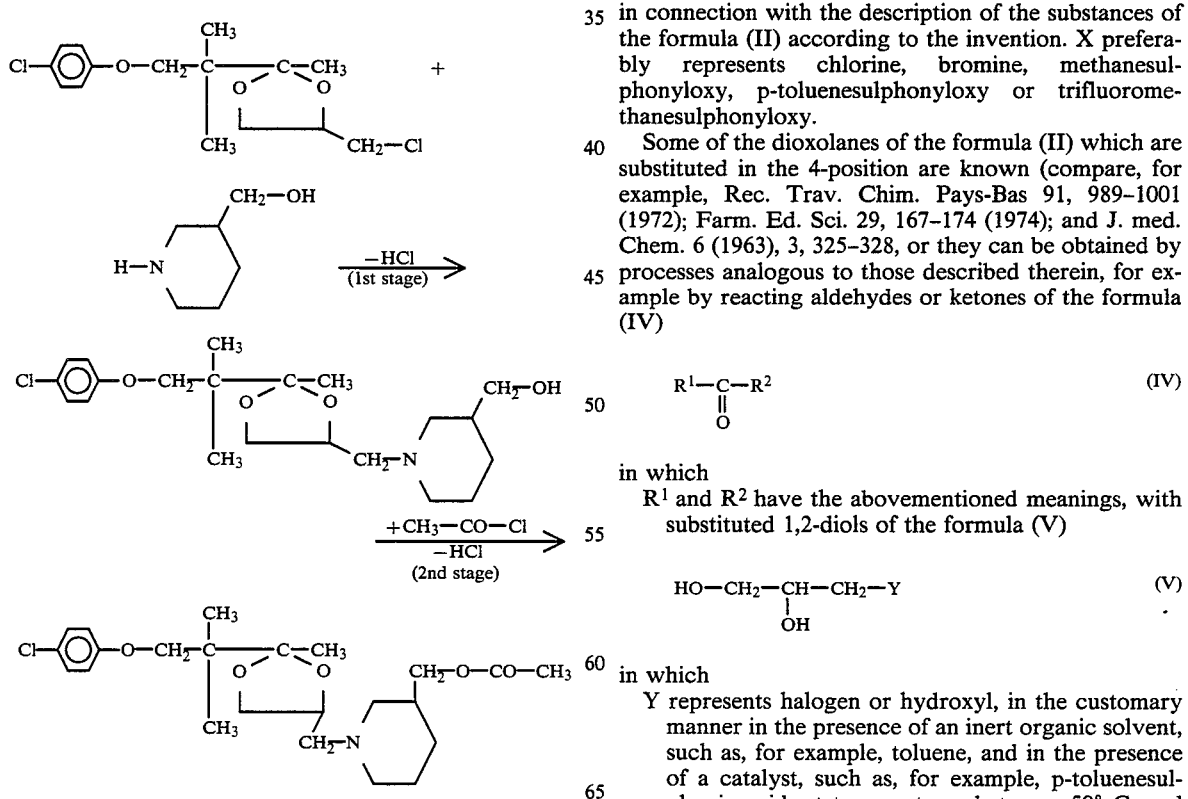

Formula (II) provides a general definition of the dioxolanes which are substituted in the 4-position and are required as starting substances for carrying out the process according to the invention. In this formula, $R^1$ and $R^2$ preferably have those meanings which have already been mentioned as preferred for these radicals in connection with the description of the substances of the formula (II) according to the invention. X preferably represents chlorine, bromine, methanesulphonyloxy, p-toluenesulphonyloxy or trifluoromethanesulphonyloxy.

Some of the dioxolanes of the formula (II) which are substituted in the 4-position are known (compare, for example, Rec. Trav. Chim. Pays-Bas 91, 989–1001 (1972); Farm. Ed. Sci. 29, 167–174 (1974); and J. med. Chem. 6 (1963), 3, 325–328, or they can be obtained by processes analogous to those described therein, for example by reacting aldehydes or ketones of the formula (IV)

$$R^1-C-R^2 \quad \text{(IV)}$$
$$\parallel$$
$$O$$

in which $R^1$ and $R^2$ have the abovementioned meanings, with substituted 1,2-diols of the formula (V)

$$HO-CH_2-CH-CH_2-Y \quad \text{(V)}$$
$$\quad\quad\quad\quad\quad\mid$$
$$\quad\quad\quad\quad\quad OH$$

in which

Y represents halogen or hydroxyl, in the customary manner in the presence of an inert organic solvent, such as, for example, toluene, and in the presence of a catalyst, such as, for example, p-toluenesulphonic acid, at temperatures between 50° C. and 120° C.; and, in cases where Y represents the hydroxyl group, reacting the resulting 4-hydroxymethyl-1,3-dioxolanes of the formula (IIa)

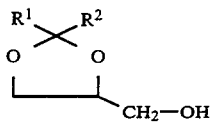

in which
R$^1$ and R$^2$ have the abovementioned meanings, with optionally substituted alkyl- or aryl-sulphonyl halides of the formula (VI)

$$Z\text{-}SO_2\text{-}Hal \qquad (VI)$$

in which
Hal represents halogen, preferably chlorine, and
Z represents optionally substituted alkyl or aryl, preferably methyl, trifluoromethyl or 4-methylphenyl,
if appropriate in the presence of a diluent, such as, for example, diethyl ether, and if appropriate in the presence of an acid-binding agent, such as, for example, pyridine or triethylamine, at temperatures between −20° C. and +100° C., to give the compounds of the formula (IIb)

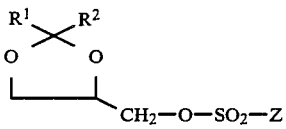

in which
R$^1$, R$^2$ and Z have the abovementioned meaning.

Ketones of the formula (IV) are known (compare, for example, DE-OS (German Published Specification) 3.210.725 or DE-OS German Published Specification) 3,048,266); they can be obtained in a simple manner by known methods.

The substituted 1,2-diols of the formula (V) and the sulphonyl halides of the formula (VI) are generally known compounds of organic chemistry.

Formula (III) provides a general definition of the hydroxymethylpiperidines also required as starting substances for the process according to the invention. Preferred compounds of the formula (III) are 2-hydroxymethylpiperidine and 3-hydroxymethylpiperidine. The hydroxymethylpiperidines of the formula (III) are known (compare, for example, Beilstein "Handbuch der organischen Chemie" ("Handbook of Organic Chemistry"), Volume 21, II, page 8).

Preferred acylating agents used for the second stage of the process according to the invention (acylation), which is to be carried out if appropriate are
(a) halides or anhydrides of the formula (VII)

$$R^4\text{-}CO\text{-}A \qquad (VII)$$

in which
R$^1$ represents alkyl, in particular methyl, ethyl or n- or i-propyl, alkoxy, in particular methoxy or ethoxy, dialkylamino, in particular dimethylamino or diethylamino, alkoxyalkyl, in particular methoxymethyl, halogenoalkyl, in particular chloromethyl, dichloromethyl or trichloromethyl, or the furyl radical and
A represents halogen, in particular fluorine, chlorine or bromine, or a radical of the formula R$^4$-CO-O—, wherein
R$^4$ has the abovementioned meanings, or
(b) isocyanates of the formula (VIII)

$$R^5\text{-}N{=}C{=}O \qquad (VIII)$$

in which
R$^5$ represents alkyl, in particular methyl or ethyl.

The acylating agents of the formulae (VII) and (VIII) are generally known compounds of organic chemictry.

Possible diluents for the 1st stage of the process according to the invention are organic solvents. These include, preferably, aromatic hydrocarbons, such as benzene, toluene or xylene; halogenated hydrocarbons, such as carbon tetrachloride or chlorobenzene; formamides, such as dimethylformamide; nitriles, such as acetonitrile or propionitrile; alcohols, such as propanol or butanol; amines, such as triethylamine or piperidine; and the highly polar solvents dimethylsulphoxide or hexamethylphosphoric acid triamide.

If appropriate, the process according to the invention (1st stage) is carried out in the presence of a base as an acid-binding agent. All the customary organic and, in particular, inorganic bases can be used here. These include, preferably, alkai metal hydroxides or carbonates, such as, for example, sodium hydroxide, sodium carbonate or potassium carbonate; and furthermore triethylamine and pyridine.

It is also possible to use an appropriate excess of hydroxymethylpiperidine of the formula (III) as the acid-binding agent.

If appropriate, the 1st stage of the process according to the invention is carried out in the presence of a catalyst. Alkali metal iodides, such as, for example, potassium iodide, are preferably used.

The reaction temperatures can be varied within a substantial range in the process according to the invention (1st stage). In general, the reaction is carried out between 50° C. and 250° C., preferably between 80° C. and 200° C.

The process according to the invention (1st stage) can be carried out under normal pressure or under increased pressure. In general, it is carried out under pressures between about 1.5 atmospheres gauge and 3 atmospheres gauge.

In carrying out the process according to the invention (1st stage), 1 to 3 mols of hydroxymethylpiperidine of the formula (III) and 1 to 3 mols of base are preferably employed per mol of substituted dioxolane of the formula (II).

The 4-(hydroxymethylpiperidinomethyl)-1,3-dioxolanes of the formula (Ia) are worked up and isolated by customary methods.

Possible diluents for the 2nd stage of the process according to the invention (acylation) to be carried out if appropriate are likewise organic solvents. These include, preferably, hydrocarbons, such as benzene, toluene, xylene or petroleum ether; halogenated hydrocarbons, such as methylene chloride, chloroform or carbon tetrachloride, nitriles, such as acetonitrile or propionitrile, or esters, such as ethyl acetate.

If appropriate, the 2nd stage of the process according to the invention (acylation) is carried out in the presence of an acid-binding agent. All the customary organic bases can be used as the acid-binding agent. Tertiary amines, such as, for example, triethylamine, N,N-dimethylaniline, dimethylaminopyridine or pyridine are preferably used. The acylation can also be carried out without an acid-binding agent.

The reaction temperatures can be varied within a substantial range in the 2nd stage of the process according to the invention (acylation). In general, the reaction is carried out between $-20°$ C. and $+100°$ C., preferably between $0°$ C. and $80°$ C.

The 2nd stage of the process according to the invention (acylation) is usually carried out under normal pressure.

For carrying out the 2nd stage of the process according to the invention (acylation), 1.0 to 1.3 mols, preferably equimolar amounts, of acylating agent, and 1.0 to 1.3 mols preferably equimolar amounts, of base are in general employed per mol of 4-(hydroxymethyl-piperidinomethyl)-1,3-dioxolane of the formula (Ia).

The end products are worked up and isolated by customary methods.

The following acids can preferably be used for the preparation of acid addition salts, which are tolerated by plants, of the compounds of the formula (I): hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydrocarboxylic acids, such as, for example, acetic acids, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents, thus, for example, as fungidides.

Fungicidal agents in plant protection are employed for combating Plasmodiphoromycetes, Oomycetes, Chytridiomycetes, Zygomycetes, Ascomycetes, Basiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the powdery mildew of barley causative organism (Erysiphe graminis) or against the yeast spot disease of barley causative organism (Pyrenophora teres), rice diseases, such as, for example, against the rice spot disease causative organism (Pyricularia oryzae) or against the Pellilularia sasakii causative organism, or vegetable diseases, such as, for example, against the brown rot of tomato causative organism (Phytophthora infestans). The active compounds according to the invention have both protective and systemic activity.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seeds, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl-naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable; for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable; for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or lactices, such as gum arabic, polyvinyl alcohol and polyvinyl acetate, and natural phospholipids, such as cephalines and lecithins, or synthetic phospholipids, can be used in the formulations. Further additives can be mineral or vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspension, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The process according to the invention may be illustrated by the following preparation examples:

PREPARATION EXAMPLES

EXAMPLE 1

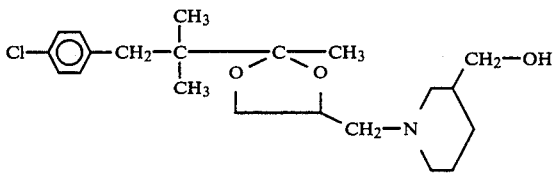

30.3 g (0.1 mol) of 4-chloromethyl-2-[1-(4-chlorophenyl)-2-methyl-prop-2-yl]-2-methyl-1,3-dioxolane, 23 g (0.2 mol) of 3-hydroxymethylpiperidine and 0.1 g of potassium iodide in 100 ml of ethanol are heated at 150° C. under pressure (2 bar) for 15 hours. For working up, the solvent is removed in vacuo, the residue is taken up in 100 ml of methylene chloride, the mixture is washed twice with 100 ml of water each time and dried over sodium sulphate and the solvent is removed again in vacuo. 38 g (100% of theory) of 2-[1-(4-chlorophenyl)-2-methyl-prop-2-yl]-4-[(3-hydroxymethylpiperidin-1-yl)-methyl]-2-methyl-1,3-dioxolane of refractive index $n^{20}$ 1.5226 are obtained.

EXAMPLE 2

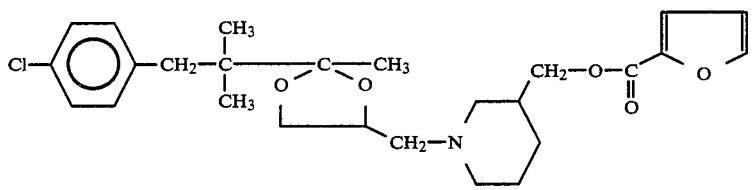

2.4 g (0.0181 mol) of furan-2-carboxylic acid chloride are added to 6.9 g (0.018 mol) of 2-[1-(4-chlorophenyl)-2-methyl-prop-2-yl]-4-[(3-hydroxymethylpiperidin-1-yl)-methyl]-2-methyl-1,3-dioxolane in 70 ml of methylene chloride at room temperature, with stirring, and stirring is continued for a further 2 hours. For working up, 50 ml of saturated sodium bicarbonate solution are added, the organic phase is separated off, the aqueous phase is extracted twice more with 50 ml of methylene chloride each time, the combined methylene chloride phases are dried over sodium sulphate and the solvent is removed in vacuo.

6 g (70% of theory) of 2-[1-(4-chlorophenyl)-2-methyl-prop-2-yl]-4-[3-(furyl-2-carbonyloxymethyl)-piperidin-1-yl-methyl]-2-methyl-1,3-dioxolane are obtained as an oil.

$1^H$-NMR (CDCl$_3$): δ=4.17 ppm (d, 2H), corresponds to the

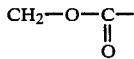

group.

PREPARATION OF THE STARTING SUBSTANCE

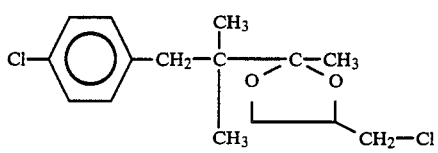

60 g (0.285 mol) of 4-(4-chlorophenyl)-3,3-dimethyl-butan-2-one, 63 g (0.57 mol) of 3-chloropropane-1,2-diol and 5.4 g (0.0285 mol) of p-toluenesulphonic acid are heated under reflux in a mixture of 500 ml of toluene and 100 ml of n-butanol for 15 hours, using a water separator. The solvent is then distilled off under a waterpump vacuum and the residue is subjected to fine distillation under a high vacuum.

After two distillations, 69 g (80% of theory) of 4-chloromethyl-2-[1-(4-chlorophenyl)-2-methyl-prop-2-yl]-2-methyl-1,3-dioxolane of boiling point 155° C. under 0.267 mbar are obtained as a cis/trans mixture.

The following compounds of the general formula (I) are obtained in a corresponding manner in accordance with the general preparation instructions:

| Example No. | R¹ | R² | (piperidine with CH₂OR³) | Refractive index ($n_D^{20}$) |
|---|---|---|---|---|
| 3 | 4-F-C₆H₄-CH₂-C(CH₃)₂- | CH₃ | 2-(HO-CH₂)-piperidinyl | 1.5173 |
| 4 | 4-F-C₆H₄-CH₂-C(CH₃)₂- | CH₃ | 3-(HO-CH₂)-piperidinyl | 1.5123 |
| 5 | 4-Cl-C₆H₄-CH₂-C(CH₃)₂- | CH₃ | 2-(HO-CH₂)-piperidinyl | 1.5269 |
| 6 | 2,4-Cl₂-C₆H₃-CH₂-C(CH₃)₂- | CH₃ | 3-(HO-CH₂)-piperidinyl | 1.5308 |
| 7 | 3,4-Cl₂-C₆H₃-CH₂-C(CH₃)₂- | CH₃ | 2-(HO-CH₂)-piperidinyl | 1.5361 |
| 8 | 3,4-Cl₂-C₆H₃-CH₂-C(CH₃)₂- | CH₃ | 3-(HO-CH₂)-piperidinyl | 1.5362 |

-continued $$\begin{array}{c} R^1 \quad R^2 \\ \diagdown / \\ \text{O} \quad \text{O} \\ | \quad | \\ \text{CH}_2 \text{—N} \underbrace{\phantom{xxx}}_{\phantom{x}} \text{CH}_2\text{—OR}^3 \end{array} \quad (I)$$

| Example No. | R¹ | R² | $-N\underbrace{\phantom{xxx}}$CH$_2$OR$^3$ | Refractive index ($n_D^{20}$) |
|---|---|---|---|---|
| 9 | 4-Cl-C$_6$H$_4$-O-CH$_2$-C(CH$_3$)$_2$- | CH$_3$ | 2-(HOCH$_2$)-piperidinyl | 1.5249 |
| 10 | 4-Cl-C$_6$H$_4$-O-CH$_2$-C(CH$_3$)$_2$- | CH$_3$ | 3-(HOCH$_2$)-piperidinyl | 1.5196 |
| 11 | 3,4-Cl$_2$-C$_6$H$_3$-O-CH$_2$-C(CH$_3$)$_2$- | CH$_3$ | 3-(HOCH$_2$)-piperidinyl | 1.5114 |
| 12 | 2-CH$_3$-C$_6$H$_4$-O-CH$_2$-C(CH$_3$)$_2$- | CH$_3$ | 3-(HOCH$_2$)-piperidinyl | Oil |
| 13 | 2-C$_2$H$_5$-C$_6$H$_4$-O-CH$_2$-C(CH$_3$)$_2$- | CH$_3$ | 3-(HOCH$_2$)-piperidinyl | 1.5041 |
| 14 | 2-Cl-5-CH$_3$-C$_6$H$_3$-O-CH$_2$-C(CH$_3$)$_2$- | CH$_3$ | 3-(HOCH$_2$)-piperidinyl | 1.5112 |
| 15 | 4-Cl-C$_6$H$_4$-CH$_2$-CH(CH$_3$)- | CH$_3$ | 3-(HOCH$_2$)-piperidinyl | 1.5273 |
| 16 | 4-Cl-3-CH$_3$-C$_6$H$_3$-O-C(CH$_3$)$_2$- | CH$_3$ | 3-(HOCH$_2$)-piperidinyl | Bp 250° C./ 0.1 mbar |

-continued $$\text{(I)}$$

| Example No. | R¹ | R² | —N⟨CH₂OR³ | Refractive index ($n_D^{20}$) |
|---|---|---|---|---|
| 17 | 2-naphthyl | CH₃ | 3-(hydroxymethyl)piperidino | Bp > 250° C./0.1 mbar |
| 18 | 3,4-dichlorophenyl-O-C(CH₃)₂- | CH₃ | 3-(hydroxymethyl)piperidino | Bp 250° C./0.1 mbar |
| 19 | 3-methylphenyl-O-CH₂-C(CH₃)₂- | CH₃ | 3-(hydroxymethyl)piperidino | Bp ~ 200° C./0.1 mbar |
| 20 | 2,4-dichlorophenyl-O-C(CH₃)₂- | CH₃ | 3-(hydroxymethyl)piperidino | Bp 250° C./0.1 mbar |
| 21 | 1-chloro-2-methoxy-6-methyl-naphthyl | CH₃ | 3-(hydroxymethyl)piperidino | Oil |
| 22 | 3-chlorophenyl-O-CH₂-C(CH₃)₂- | CH₃ | 3-(hydroxymethyl)piperidino | Bp ~ 200° C./0.1 mbar |
| 23 | 2-methylphenyl-O-CH₂-C(CH₃)₂- | CH₃ | 3-(hydroxymethyl)piperidino | Oil |
| 24 | 3-trifluoromethylphenyl-O-C(CH₃)₂- | CH₃ | 3-(hydroxymethyl)piperidino | $n_D^{20}$ 1.4810 |

-continued

| Example No. | R¹ | R² | $-N\langle \rangle CH_2OR^3$ | Refractive index ($n_D^{20}$) |
|---|---|---|---|---|
| 25 | 1,4-dimethoxynaphthyl | CH₃ | 3-(CH₂—OH)piperidinyl | Oil |
| 26 | 4-chloro-3-methylphenoxy-CH₂-C(CH₃)₂- | CH₃ | 3-(CH₂—OH)piperidinyl | Oil |

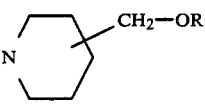

USE EXAMPLES

The compounds shown below are used as comparison substances in the following use examples:

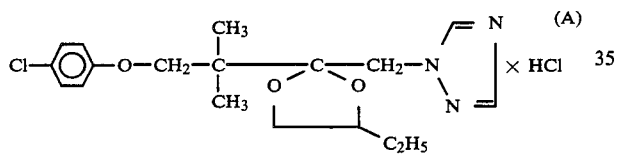

2-[1-(4-Chlorophenoxy)-2-methyl-prop-2-yl]-4-ethyl-2-(1,2,4-triazol-1-yl-methyl)-1,3-dioxolane hydrochloride and

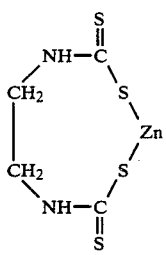

ps zinc ethylene-1,2-bis-(dithiocarbamate)

EXAMPLE A

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compound according to preparation Example 1.

EXAMPLE B

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe gramins f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 1, 3, 4 and 10.

EXAMPLE C

Pyricularia test (rice)/systemic
Solvent: 12.5 parts by weight of acetone
Emulsifier: 0.3 parts by weight of alkylaryl polyglycolether To produce a suitable preparation of active compound, 1 part by weight of active compound is mixed with the stated amount of solvent and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1, 4 and 10.

We claim:

1. A substituted 4-piperidinomethyl-1,3-dioxolane of the formula

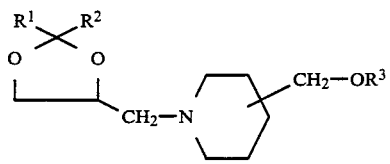

in which $R^1$ is tetrahydronaphthyl, decahydronaphthyl, or naphthyl which is optionally mono- to hepta-substituted by substituents independently selected from the group consisting of hydroxyl, halogen, and alkyl, alkoxy, alkenyloxy, alkinyloxy and alkanoyloxy with in each case 1 to 4 carbon atoms in the alkyl part; cycloalkyl or cycloalkenyl with 3 to 7 carbon atoms and optionally substituted by alkyl with up to 4 carbon atoms; optionally substituted phenyl, phenylalkyl, phenoxyalkyl or phenylthioalkyl with in each case up to 6 carbon atoms in the alkyl part when present, optional substituents on the phenyl nucleus when present being independently selected from the group consisting of hydroxyl, halogen, cyano, nitro, alkyl, alkoxy, alkenyloxy, alkinyloxy and alkylthio with in each case up to 4 carbon atoms, halogenoalkyl, halogenoalkoxy and halogenoalkylthio with in each case 1 or 2 carbon atoms and 1 to 5 identical or different halogen atoms, cycloalkyl with 5 to 7 carbon atoms, alkoxycarbonyl and alkanoyloxy with in each case up to 4 carbon atoms in the alkyl part, phenyl and phenoxy optionally substituted by halogen or by alkyl with up to 4 carbon atoms, and the radical R-O-N=CH—, R being alkyl, alkenyl or alkinyl in each case with up to 4 carbon atoms; or is cyclohexylalkyl, cyclohexyloxyalkyl or cyclohexylthioalkyl with in each case up to 6 carbon atoms in the alkyl part and in each case optionally substituted in the cyclohexyl part by alkyl radicals with up to 4 carbon atoms, $R^2$ is hydrogen or methyl, and $R^3$ is hydrogen or a radical of the formula $$R^4-\underset{\underset{O}{\|}}{C}-$$

wherein $R^4$ is alkyl, alkoxy or alkylamino or dialkylamino with in each case 1 to 6 carbon atoms in the individual alkyl parts, alkoxyalkyl with in 1 to 6 carbon atoms in each alkyl part, halogenoalkyl with up to 6 carbon atoms and up to 5 halogen atoms, or furyl.

2. A compound or addition product according to claim 1, in which $R^1$ is tetrahydronaphthyl, decahydronaphthyl, or naphthyl which is optionally mono-, di or tri-substituted by substituents independently selected from the group consisting of fluorine, chlorine, bromine, iodine, hydroxyl, methyl, ethyl, methoxy, ethoxy, allyloxy, propargyloxy and acetoxy, or is cycloalkyl or cycloalkenyl with 5 to 7 carbon atoms optionally mono-, di or tri-substituted by methyl and/or ethyl, or is phenyl which is optionally mono-, di or tri-substituted by substituents, or is a radical of the formula

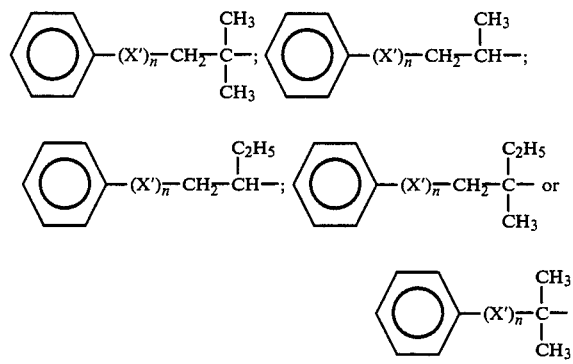

which is optionally mono-, di- or tri-substituted in the phenyl nucleus, possible substituents on the various phenyl nuclei being selected from the group consisting of hydroxyl, fluorine, chlorine, bromine, iodine, cyano, nitro, methyl, methoxy, methylthio, ethyl, ethoxy, ethylthio, n- and i-propyl, isopropoxy, n-, i-, s- and t-butyl, allyloxy, propargyloxy, trifluoromethyl, trifluoromethoxy, trifluoromethylthio, cyclohexyl, methoxycarbonyl, ethoxycarbonyl, acetoxy, and phenyl and phenoxy which are optionally substituted by fluorine, chlorine and/or methyl, or is R-O-N=CH- in which R is methyl, ethyl, n- or i-propyl, n-, i-, s- or t-butyl, allyl or propargyl; or, in addition is a radical of the formula

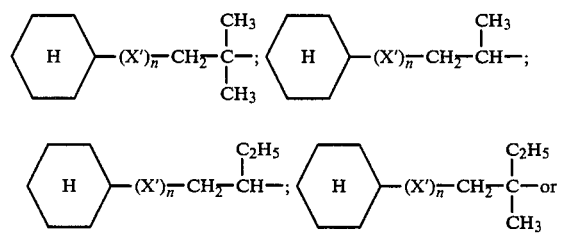

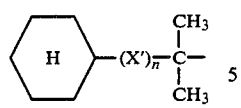

which is optionally mono- to tri-substituted in the cyclohexyl part by methyl, ethyl and/or isopropyl, wherein X' is oxygen or sulphur, n is 0 or 1 and the cyclohexyl moiety is optionally mono-, di- or tri-substituted by methyl, ethyl and/or isopropyl, $R^2$ is methyl, and $R^3$ is hydrogen or a radical of the formula

wherein $R^4$ is methyl, ethyl, n- or i-propyl, chloromethyl, dichloromethyl, trichloromethyl, methoxy, ethoxy, methylamino, ethylamino, dimethylamino, diethylamino or furyl.

3. A compound according to claim 1, wherein such compound is 2-[1-(4-chlorophenyl)-2-methyl-prop-2-yl]-4-[(3-hydroxymethylpiperidin-1-yl)-methyl]-2-methyl-1,3-dioxolane of the formula

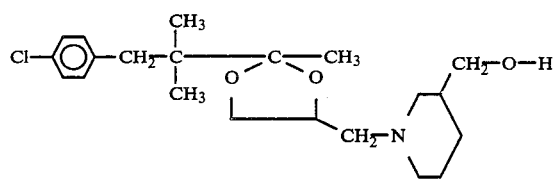

or a plant-tolerated addition product thereof with an acid or metal salt.

4. A compound according to claim 1, wherein such compound is 2-[1-(4-fluorophenyl)-2-methyl-prop-2-yl]-4-[(3-hydroxymethylpiperidin-1-yl)-methyl]-2-methyl-1,3-dioxolane of the formula

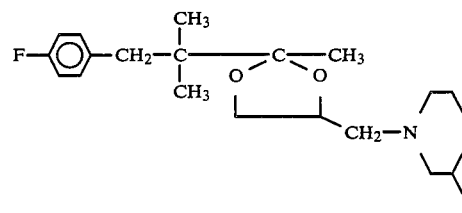

or a plant-tolerated addition product thereof with an acid or metal salt.

5. A compound according to claim 1, wherein such compound is 2-[1-(4-chlorophenoxy)-2-methyl-prop-2-yl]-4-[(3-hydroxymethylpiperidin-1-yl)-methyl]-2-methyl-1,3-dioxolane of the formula

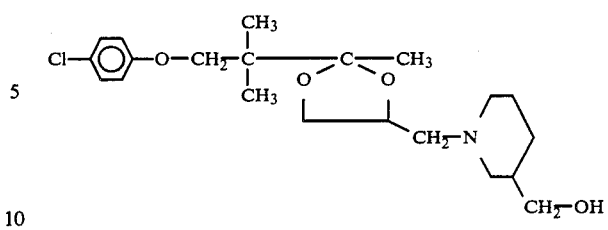

or a plant-tolerated addition product thereof with an acid or metal salt.

6. A compound according to claim 1, wherein such compound is 2-[1-(3,4-dichlorophenoxy)-2-methyl-prop-2-yl]-4-[(3-hydroxymethylpiperidine-1-yl)-methyl]-2-methyl-1,3-dioxolane of the formula

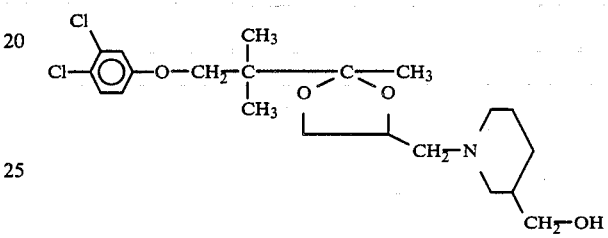

or a plant-tolerated addition product thereof with an acid or metal salt.

7. A compound according to claim 1, wherein such compound is 2-[1-(2-methylphenoxy)-2-methyl-prop-2-yl]-4-[(3-hydroxymethylpiperidin-1-yl)-methyl]-2-methyl-1,3-dioxolane of the formula

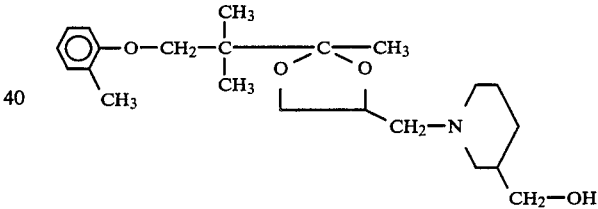

or a plant-tolerated addition product thereof with an acid or metal salt.

8. A compound according to claim 1, wherein such compound is 2-[1-(2-ethylphenoxy)-2-methyl-prop-2-yl]-4-[(3-hydroxymethylpiperidin-1-yl)-methyl]-2-methyl-1,3-dioxolane of the formula

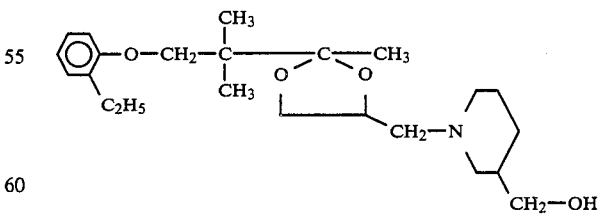

or a plant-tolerated addition product thereof with an acid or metal salt.

9. A compound according to claim 1, wherein such compound is 2-[1-(2-chloro-5-methylphenoxy)-2-methyl-prop-2-yl]-4-[(3-hydroxymethylpiperidin-1-yl)-methyl]-2-methyl-1,3-dioxolane of the formula

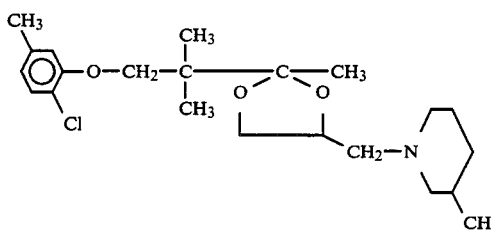

or a plant-tolerated addition product thereof with an acid or metal salt.

10. A fungicidal composition comprising a fungicidally effective amount of a compound or addition product according to claim 1 in admixture with a diluent.

11. A method of combating fungi which comprises administering to such fungi or to a habitat thereof a fungicidally effective amount of a compound or addition product according to claim 1.

12. The method according to claim 11, wherein such compound is

2-[1-(4-chlorophenyl)-2-methyl-prop-2-yl]-4-[(3-hydroxymethylpiperidin-1-yl)-methyl]-2-methyl-1,3-dioxolane, 2-[1-(4-fluorophenyl)-2-methyl-prop-2-yl]-4-[(3-hydroxymethylpiperidin-1-yl)-methyl]-2-methyl-1,3-dioxolane, 2-[1-(4-chlorophenoxy)-2-methyl-prop-2-yl]-4-[(3-hydroxymethylpiperidin-1-yl)-methyl]-2-methyl-1,3-dioxolane, 2-[1-(3,4-dichlorophenoxy)-2-methyl-prop-2-yl]-4-[(3-hydroxymethylpiperidin-1-yl)-methyl]-2-methyl-1,3-dioxolane, 2-[1-(2-methylphenoxy)-2-methyl-prop-2-yl]-4-[(3-hydroxymethylpiperidin-1-yl)-methyl]-2-methyl-1,3-dioxolane, 2-[1-(2-ethylphenoxy)-2-methyl-prop-2-yl]-4-[(3-hydroxymethylpiperidin-1-yl)-methyl]-2-methyl-1,3-dioxolane, or 2-[1-(2-chloro-5-methylphenoxy)-2-methyl-prop-2-yl]-4-[(3-hydroxymethylpiperidin-1-yl)-methyl]-2-methyl-1,3-dioxolane, or a plant-tolerated addition product thereof with an acid or metal salt.

* * * * *

UNITED STATES PATENT AND TRADEMARK OFFICE
CERTIFICATE OF CORRECTION

PATENT NO. : 4,563,447

DATED : January 7, 1986

INVENTOR(S) : Wolfgang Kramer, et al.

It is certified that error appears in the above-identified patent and that said Letters Patent is hereby corrected as shown below:

| | |
|---|---|
| Col. 1, line 47 | After "isomers" delete "for" and substitute --or-- |
| Col. 1, line 58 | Middle of formula delete "$CH_2$_" |
| Col. 4, line 6 | Correct spelling of "propargyloxy" |
| Col. 19, line 60 | Delete "$R^1$" and substitute --$R^4$-- |
| Col. 21, line 27 | Correct spelling of "hydroxycarboxylic" |
| Col. 21, line 64 | Correct spelling of "fungicides" |
| Col. 21, line 66 | Correct spelling of "plasmodiophoromycetes" |
| Col. 21, lines 66, 67 | Correct spelling of "Basidiomycetes" |
| Col. 22, lines 55, 56 and Col. 22, line 67 | After "suitable" delete ";" and substitute --:-- |
| Col. 28-32, Examples 16-26 | Delete heading of last column to wit "Refractive index ($n_D 20$)" and substitute --Physical dates-- |
| Col. 34, line 1 | Delete formula and substitute $$-- R^4-\overset{\overset{\displaystyle C}{\|}}{C} - --$$ |

UNITED STATES PATENT AND TRADEMARK OFFICE
CERTIFICATE OF CORRECTION

PATENT NO. : 4,563,447

DATED : January 7, 1986

INVENTOR(S) : Wolfgang Kramer, et al.

It is certified that error appears in the above-identified patent and that said Letters Patent is hereby corrected as shown below:

Col. 36, line 16   Correct spelling of "hydroxymethyl-piperidin"

Signed and Sealed this

Thirteenth Day of May 1986

[SEAL]

Attest:

DONALD J. QUIGG

Attesting Officer   Commissioner of Patents and Trademarks